United States Patent [19]

Piasio et al.

[11] 4,197,287
[45] Apr. 8, 1980

[54] METHOD AND APPARATUS FOR PERFORMING IN NITRO CLINICAL DIAGNOSTIC TESTS USING A SOLID PHASE ASSAY SYSTEM HAVING SPECIAL UTILITY FOR USE WITH AUTOMATIC PIPETTING EQUIPMENT

[75] Inventors: Roger N. Piasio, Yarmouth; David A. Perry, Portland, both of Me.; Pangal N. Nayak, Belmont, Mass.

[73] Assignee: Ventrex Laboratories Inc., Portland, Me.

[21] Appl. No.: 805,431

[22] Filed: Jun. 10, 1977

[51] Int. Cl.$^2$ .................... A61K 39/00; G01N 31/06; G01N 33/16
[52] U.S. Cl. .................... 424/1; 23/230 B; 23/230.6; 23/915; 23/920; 422/58; 422/71; 422/102; 424/12; 435/7; 435/296
[58] Field of Search ............... 23/230 B, 253 R, 259, 23/259 R, 253 TP, 292; 73/23.1; 210/23 C, 198 C; 424/1, 1.5 R, 12; 428/36, 305, 318; 195/63, 68, 127, 103.5 A; 422/58, 69, 59, 70, 102, 71

[56] References Cited
U.S. PATENT DOCUMENTS

| | | | |
|---|---|---|---|
| 3,206,602 | 9/1965 | Eberle | 23/230 B |
| 3,298,527 | 1/1967 | Wright | 210/198 C |
| 3,464,798 | 9/1969 | Kilthau | 23/253 R |
| 3,646,346 | 2/1972 | Catt | 23/230 B |
| 3,652,761 | 3/1972 | Weetall | 424/12 |
| 3,770,384 | 11/1973 | Brumfield | 23/258.5 B |
| 3,826,619 | 7/1974 | Bratu et al. | 23/253 R |
| 3,867,517 | 2/1975 | Ling | 424/1 |
| 3,879,262 | 4/1975 | Schuurs | 424/12 X |
| 3,896,217 | 7/1975 | Johnson | 424/1 |
| 3,933,965 | 1/1976 | Gallone et al. | 428/36 X |
| 3,951,748 | 4/1976 | Devlin | 424/12 X |
| 3,972,529 | 8/1976 | McNeil | 428/36 X |
| 3,999,948 | 12/1976 | Deindoerfer | 23/230 B |
| 4,020,151 | 4/1977 | Bolz | 23/230 B X |
| 4,031,197 | 6/1977 | Marinkovich | 23/230 B X |
| 4,034,072 | 7/1977 | Mjos et al. | 23/230 B |
| 4,111,754 | 9/1978 | Park | 422/99 X |
| 4,116,638 | 9/1978 | Kenoff | 422/99 X |

OTHER PUBLICATIONS

A Solid Phase Radioassay for Plasminogen in Human Plasma; Schmer et al., Univ. of Wash. Publication.
Methodological Principles of the Capillary Radioimmunoassay, Friedel; Clin. Chem. 21, 967 (1975).
Keane, P. M., Walker; Thermodynamic Aspects of Some Radioimmunoassays, Clin. Chem. 22, 70 (1976).
SPAC Advertisement.

Primary Examiner—Michael S. Marcus

[57] ABSTRACT

A method and solid phase matrix is disclosed which has special utility for use in conjunction with automatic pipetting apparatus for conducting reactions at a liquid-solid interface. A reaction component is fixed on the surface of the solid phase matrix which is wetted by a liquid phase containing a freely diffusing, mobile component. The matrix is comprised of a support surface to which are attached a plurality of inwardly projecting fins. The innermost extension of the fins defines a centrally located well into which an automatic pipetting apparatus may be inserted. The method may be used for qualitative or quantitative determinations of the mobile component contained in a liquid which wets the solid phase matrix.

12 Claims, 6 Drawing Figures

METHOD AND APPARATUS FOR PERFORMING IN NITRO CLINICAL DIAGNOSTIC TESTS USING A SOLID PHASE ASSAY SYSTEM HAVING SPECIAL UTILITY FOR USE WITH AUTOMATIC PIPETTING EQUIPMENT

BACKGROUND OF THE INVENTION

1. Field of the Invention

The invention relates to a method and associated apparatus for performing solid phase assays having special utility for use in conjunction with automatic pipetting equipment.

2. Description of the Prior Art

In recent years, numerous techniques have been employed in the area of laboratory diagnostics to simplify operating procedures of existing methods and to provide new methods of improved speed, sensitivity and accuracy. In particular, solid phase reactions have been especially valuable in simplifying the manipulations of prior art procedures and making possible procedures that could not be performed with conventional homogeneous phase reactions. However, solid phase assay techniques heretofore have suffered from the disadvantage of requiring hand manipulation of small volumes which inherently are subject to a wide range of laboratory error.

A solid phase reaction is generally carried out between one reactant, the fixed component, immobilized on the surface of an insoluble support, and a second reactant, the mobile component, in solution. The reaction occurs when a molecule or molecular arrangement of the mobile reactant, in the course of diffusion, collides with a molecule of the fixed reactant immobilized on the surface of the solid support matrix. The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of fixed component unbound, in the case of an immunochemical reaction.

Any conventional chemical reaction or enzyme-catalyzed reaction resulting in a directly or indirectly measurable change can, in principle, be carried out by solid phase techniques. Direct measurable changes include changes of pH, light absorbance in the visible and ultraviolet regions or changes in fluorescence intensity. Indirect measurements can be made whenever the primary reactants or products are not readily measurable themselves by interposing the action of a reagent to carry out further reaction steps resulting in a measurable change and by the introduction of specific separation techniques. Such strategies may be employed alone or in combinations, as is understood in the art.

Where the reaction consists solely of binding, in the absence of chemical change, techniques developed in the field of immunochemistry may be used to measure the extent of the reaction. Solid phase reactions are especially suited for immunochemical assays because the reactants in bound form may readily be removed from the solution by virtue of their attachment to the solid phase. Frequently, however, the components bound in an immunochemical reaction cannot be directly measured because they are indistinguishable by chemical methods from other substances commonly present in the same reaction mixture so that the mere disappearance of a reactive component from solution or its accumulation on the solid phase cannot be measured directly. Therefore, additional steps are taken in order to make a measurable change related to the amount of binding.

The variety of approaches taken by workers in the prior art can be grouped into two general categories. In the first of these, termed competitive or indirect immunoassays, the immobilized component is present in controlled amount and the mobile component present in unknown amount. To the unknown amount of mobile component is added a known amount of the same component which has been tagged by the addition of a measurable substituent which does not interfere with its immunochemical reactive properties. The tag may consist of a radioisotope, a chromophore, a fluorophor or an enzyme. The amount of tagged material bound immunochemically to the solid phase will depend upon the amount of untagged component in solution competing for the same binding sites. The more of the unknown present, the less will be the amount of tagged component bound.

In the second general method, termed the sandwich method or direct method, the solid phase containing an amount of immunochemically bound mobile component resulting from the first immunochemical reaction is subjected to the action of a reagent which can also bind immunochemically to the solid phase, but only at sites already occupied by the immunochemically bound mobile component. The reagent may be tagged, for example, as in the first method with a radioisotope, a fluorophor, a chromophore or an enzyme. The amount of tagged reagent bound is a direct measure of the amount of mobile component bound, which in turn is a measure of the amount of mobile component initially present in the reaction mixture. Where the tag is a radioisotope, the technique, whether competitive or noncompetitive, is termed a radioimmunoassay. When the tag is an enzyme, the assay is termed an enzyme immunoassay.

Other kinds of solid phase reactions of the type generally described hereinabove are presented by way of example. The immunoradiometric assay for quantitative determination of an antigen is conducted by first reacting a known excess of labeled antibody with the unknown amount of antigen in a homogeneous phase reaction. Subsequently, immobilized antigen in excess amount is added in order to bind the unreacted soluble labeled antibody. The amount of unknown antigen is determined by measuring the difference between the total labeled antibody and the amount bound to the solid phase. The method gives direct quantitative resuls only with univalent antigen, i.e., antigen which can only bind one molecule of antibody.

Enzyme-catalyzed reactions are conveniently carried out in solid phase systems. An enzyme immobilized on a solid phase matrix may be used to quantitatively assay for, or qualitatively detect the presence of, the substrate for the enzyme in a sample of biological material. For example, lactic acid in serum may be measured using a matrix coated with lactic dehydrogenase. Similarly, urea may be assayed using a solid phase insert bearing immobilized urease. In additional to clinical applications, enzyme assays may be used for quality control monitoring of industrial process steps and also for carrying out process steps. As an example of the former, immobilized penicillinase could be employed in an assay to monitor the quality of penicillin produced during the process of manufacturing the drug. As an example of the latter, immobilized proteases or nucleuses could be useful to remove or inactivate contaminating proteins or nucleic acids.

The presence of an enzyme of clinical significance in a sample of biological material may also be assayed by providing a substrate for the enzyme immobilized on a solid phase matrix. An example of an assay which could be adapted for use in this fashion is the method disclosed in U.S. patent application Ser. No. 795,497 of James W. Ryan and Alfred Chung. A lysozyme assay, in which radioactively labeled Micrococcus lysodeikticus is covalently bound to the surface of a solid phase matrix, further exemplifies the use of an immobilized substrate in an enzyme reaction.

Further examples of useful solid phase reactions are provided by the specific binding reactions of certain proteins. These include, for example, beta-lactoglobulin, which specifically binds folic acid, specific receptor proteins capable of binding hormones, such as the receptor substance purified from rat mammory tumor cells which specifically binds prolactin and the variety of plant proteins such as concanavalin A, which are capable of specifically binding certain carbohydrates.

Conventional chemical reactants may be designed for use in solid phase reactions. Solid phase reactants capable of forming colored complexes, as by the formation of glycosyl derivatives or by diazo coupling to a reagent immobilized on the surface of a solid phase matrix could be devised for use, either alone or in combination with an enzyme-catalyzed reaction, to provide for a color change on the surface of the matrix. Also, ion exchange reactions may conveniently be conducted using a solid phase matrix of the present invention. The foregoing examples are illustrative only and additional possibilities will be apparent to those having ordinary skill in the appropriate art.

In such solid phase technology, the reagent or reagents used in the procedure are immobilized by being coated or bonded, either covalently or by adsorption to the solid phase material, which is then wetted by the sample to be tested. The manner of coupling such reagents to the solid phase material is known. See, for example, the disclosures in U.S. Pat. No. 3,652,761, No. 3,879,262 and No. 3,896,217.

Examples of commonly used slid phase materials include, but are not limited to, glass or polymeric tubes which are coated with the reagent or reagents on their internal surfaces; polymeric coated sticks; micro and macro beads formed of polymers and of glass and porous matrices.

U.S. Pat. No. 3,826,619 discloses a solid phase matrix used for qualitative testing. The disclosed matrix differs substantially from that of the present invention. First, it may only be used to detect the presence or absence of antigens and not for measuring the quantity of antigens like the present invention. Second, the physical form of the matrix as exemplified by FIG. 5 of U.S. Pat. No. 3,826,619 is not suitable for use in conjunction with automatic pipetting equipment because there is no place for the automated insertion of a fluid dispensing device such as in the present invention. Moreover, the disclosed matrices have never been commercially used.

Coated tubes are exemplified by the Immunotube TM system marketed by Smith Kline Instruments of Sunnyvale, Calif.; the Rianen TM system of New England Nuclear, North Billerica, Mass.; the SPAC TM system of Mallinkrodt of St. Louis, Mo.; and the tubes described in U.S. Pat. No. 3,867,517 issued Feb. 18, 1975 to Ling.

The StiQ TM matrix of International Diagnostic Technology Co. of Santa Clara, Calif. is a widely used stick type solid phase matrix.

The Biological Products Division of Corning Glass Works in Medfield, Mass., markets the Immo Phase TM system which exemplifies the coated bead system.

Immunochemical assays are highly useful in clinical research and diagnosis. They are highly specific, owing to the highly selective nature of antigen-antibody reactions. The antigen-antibody binding is very tight so that once the binding reaction has had an opportunity to occur, the limit of detectability is determined by the measurability with which the tag can be detected. Immunochemical assays are exceedingly versatile, owing to the fact that they can be used to measure substances which lack any measurable chemically distinguishable features. Because of these desirable attributes, there has been considerable interest in improving the ease of manipulation, sensitivity and applicability of immunochemical assays. The development of solid phase immunoassays has been one of the major advances in the field.

When small volume samples are used, laboratory errors are introduced because control conditions such as pH and volume in the sample are hard to maintain and because it is difficult to insure that the solid phase is uniformly wetted during every similar assay.

As previously stated, the solid phase systems currently being used employ coated tubes, coated sticks, coated beads and sponges as solid phase configurations.

The introduction of solid phase technology has permitted the performance of novel procedures that were heretofore extremely difficult using free solution technology. An exemple of this is the sandwich assay technique described hereinabove. To be carried out in homogeneous solution, the sandwich technique would require a large excess of one of the reactants. More importantly, separation of the first antigen-antibody complex from a homogeneous phase solution requires the use of sophisticated physical-chemical techniques, especially if the antigen is relatively small compared to the antibody and molecular weight differences between free antibody and complexed antibody are slight. In contrast, the separation procedure in a solid phase system is a matter of the utmost simplicity. As will be described below, one of the primary advantages of solid phase technology, the ease of separating the solid and liquid phases, is maximized in the practice of the present invention, which provides extremely simple means for separating the phases.

While, in theory, solid phase technology offers numerous advantages over free solution or homogeneous systems, it does have certain limitations due principally to the solid phase configurations heretofore used. For example, since at least one of the reagents in a solid phase system is effectively immobilized by being bound to the surface, the reaction rate of solid phase systems is generally slower than that of homogeneous or free solutions systems. Additionally, there is normally a maximum amount of reagent which can be bound to the solid phase surface, the maximum amount being generally dependent upon the surface area, the purity of the reagent and the specific procedure used to bind the reagent to the surface. Optimally, as much as possible of the surface area of the solid material should be coated so as to increase the reaction rate and decrease the reaction time.

The earliest solid phase systems devised were test tubes coated on the inside surface. Commercial examples of coated tube technology include the Immunotube TM system marketed by Smith Kline Instruments of Sunnyvale, Calif., and the Rianen TM system of New England Nuclear, North Billerica, Mass., and the tubes described in U.S. Pat. No. 3,867,517 issued Feb. 18, 1975 to Ling. Although coated tube systems have proven useful for immunoassay purposes, they fail to exploit the full range of potential advantages offered by solid phase systems. A principal disadvantage is that the surface to volume ratio is relatively low and reaction kinetics may be further hindered by the fact that the reactive surface is located at the boundary of the solution volume, which may be relatively remote from the main body of the solution. Therefore, the average distance between mobile reactants and the reactive surface is large. In addition, each test tube must be coated separately and this constraint is likely to result in variations from tube to tube in the amount of coating material applied and ultimately in the assay results. It is also relatively expensive. Reactions conducted in coated tubes are subject to errors caused by convection in the reaction fluid. Results varying as much as 10-fold can be caused by convection in these systems.

Attempts to improve on the performance of coated tubes have led to a variety of systems designed to increase the surface to volume ratio of the solid phase system. These methods have included providing highly convoluted surfaces, reducing the volume of liquid required and providing surfaces of finely divided material.

The SPAC TM system of Mallinkrodt Chemical Company is basically a coated tube system which exemplifies the strategy of providing a convoluted surface to increase surface area in the coated tube format. Additionally, the tubes are provided with a detachable lower section which may be batch coated to achieve greater uniformity from tube to tube. A consequence of the batch immobilization on coated tube bottoms is that the outsides as well as the insides of the tubes become coated. This makes it difficult for the laboratory technician to work with the tubes without coming into contact with whatever material is coated on their surface and valuable immunological reactants are wasted. The convoluted surface area is said to increase by 3-4 times the amount of reactive surface available. However, the reactive surface remains at the periphery of the solution, which may be suboptimal geometry from the standpoint of the average diffusion distance from the solution to the reaction surface. Due to the complexity of the surface, difficulties in washing the surface free of contaminating substances may be encountered. As with coated tube systems in general, the SPAC TM system is likely to be sensitive to convection currents which can result in large errors as previously described. Convection may be reduced by carrying out the reaction in a constant temperature bath. However, this procedure presents additional equipment requirements for the clinical laboratory. For measurement of hapten antigens, the system is additionally suboptimal if the reaction is carried out at 37° C. according to the manufacturer's recommendation. It has been shown that increasing the temperature of certain antibody-hapten reactions tends to enhance the rate of dissociation of the antibody-hapten complex relative to the rate of its formation. See Smith, T. W. and Skubitz, K. M., *Biochemistry* 14, 1946, (1975) and Keane, P. M., Walker, W. H. C., Gauldie, J. and Abraham, G. E., *Clin. Chem.* 22, 70 (1976).

One system which affords a high surface area for over-all volume is the coated micro glass bead system as, for example, the Immo Phase TM system of Corning Glass Works. This system exemplifies the use of finely divided particles. It provides a high coated surface area with a correspondingly high reaction rate. Due to settling of the particles during the reaction, optimization of test systems of this kind requires that the test tubes in which they are placed during reaction be capped and mixed vertically during the reaction to insure that all surfaces come in contact with the reactants. Further, the use of particles necessitates multiple centrifugations and washings to completely separate the immobilized product from tne solution reactants. Glass particle surfaces have the further disadvantage that there is greater nonspecific protein binding to glass, as compared to plastic.

Coated tubes, wherein the reagents are coated covalently or by adsorption on the inner surfaces thereof, (as described, for example, in U.S. Pat. No. 3,867,517, issued Feb. 18, 1975 to Ling) are easy to use. They offer a more limited surface area than the present invention and their correspondingly slow reaction time may decrease the specificity of the prescribed test procedure.

A third type of solid phase insert matrix is represented by the StiQ TM assay of International Diagnostic Technology Corporation, Santa Clara, Calif., designed to exploit a solid phase assay disclosed in U.S. Pat. No. 4,020,151, issued Apr. 26, 1977 to Bolz, et al. In this system, a disc shaped, uncoated insert matrix of material capable of adsorbing proteins from serum is provided. In this system, the limitations are not only due to surface to volume ratio or geometric considerations but are mainly due to problems associated with the initial adsorption step: the presence of interfering substances and the difficulty of obtaining measurable adsorption of components present in low concentration.

Sponge-like matrices, while offering relatively large surface areas, are difficult to wash thoroughly at the conclusion of the reaction time, thus making separation extremely difficult. See U.S. Pat. No. 3,951,748 issued Apr. 20, 1976 to Devlin. U.S. Pat. No. 3,464,798 issued Sept. 2, 1969 to Kilthau discloses a combination of a receptacle and a closely-fitting insert matrix, so shaped as to squeeze the reaction fluid into a thin layer between the container walls and the matrix surface.

Another possibly pertinent patent, though not employing a solid phase matrix is U.S. Pat. No. 3,206,602 issued Sept. 14, 1965 to Eberle.

SUMMARY OF THE INVENTION

The present invention relates to a solid phase matrix for use in chemical, enzymatic and immunochemical assaying techniques which has special utility in conjunction with automatic pipetting equipment. The matrix may also be used for conventional hand manipulated batch analysis.

The present invention also relates to a process of using the solid phase matrix of the invention for both quantitative and qualitative assays.

The solid phase matrix has a closed support surface which defines a well-like volume in which a fluid sample may be disposed when the matrix is placed in a fluid receptacle such as a test tube. A plurality of inwardly projecting members are preferably formed as a unitary part of the inside of the closed support surface. The innermost extension of the projecting members defines a centrally disposed cylindrical region into which may be inserted an automatic pipetting device for aspirating and dispensing fluid samples.

The support surface defines a top and bottom opening. The top opening permits the ingress and egress of the probe of the automatic pipetting apparatus. The bottom opening permits entry of fluid into the region during incubation of the fluid sample. If the bottom of the test tube is curved, the projecting members may be rounded to extend into the bottom hemispherical section of the test tube to promote more intimate contact of the matrix with the fluid sample. Alternatively, the bottom opening of the support surface may be closed to define a fluid receptacle consisting of the support surface and a bottom section. This embodiment eliminates the need for a test tube to retain the fluid sample.

Another embodiment of the solid phase matrix has a plurality of concentric support surfaces joined together by the inward projecting members. The innermost support surface defines a well-like volume into which may be inserted an automatic pipetting device for aspirating and dispensing fluid samples.

The process of the invention may be utilized for quantitative or qualitative assays. A fixed component is bound on the surface of the solid phase matrix of the invention in accordance with the prior art techniques discussed, supra. A fluid sample which contains a mobile component that is to be assayed is incubated in contact with the solid phase matrix for a given period of time. The process of the present invention employs a reaction volume sufficiently large to permit a serum sample to be diluted with buffer to control pH and reduce errors due to variation in the sample pH or other factors such as protein concentration. Thereafter, the reaction of the mobile component of the fluid sample with the fixed component is detected either quantitatively or qualitatively by techniques that vary with the type of reactants as described, supra.

An automatic pipetting apparatus may be used to aspirate and dispense fluid samples by insertion of a probe into the centrally disposed cylindrical volume of the solid phase matrix. Thereafter, the reaction of the mobile component of the fluid sample with the fixed component is detected either quantitatively or qualitatively by techniques that vary with the reactants as described above.

The invention has distinct advantages over the prior art. The configuration of the solid phase matrix with a centrally disposed volume allows presently available commercial automatic pipetting apparatus to be used to rapidly transfer precisely metered volumetric samples to and from contact with the fixed component. Moreover, the automatic pipetting apparatus may be used to buffer or dilute small volume samples to provide a precisely metered larger and constant test volume prior to reacting the fixed and mobile components. The relative increase of coated surface area over certain types of prior art solid phase systems makes it possible to conduct quantitative determinations over a wider range of mobile reactant concentrations due to enhanced sensitivity at the lower end of the concentration range and increased binding capacity such that proportionate response is possible at high concentrations of the mobile reactant. Higher surface area also increases the speed and reliability of qualitative "yes, no" tests. Additionally, the use of the solid phase matrix of the present invention makes it possible to carry out quantitative analyses in a reaction volume of the order of a few milliliters, in contrast to prior art methods such as those disclosed in U.S. Pat. No. 3,464,798 in which the surface to volume ratio is increased by decreasing the total reaction volume to a microliter or smaller scale. Errors due to timing are also reduced because the increased forward reaction rate results in more rapid approach to equilibrium. As the reaction approaches equilibrium, the reaction rate tends to decrease so that errors induced by stopping the reaction will be less significant. Assays for detecting any given type of mobile component which are conducted in accordance with the invention may be readily standardized as to time of reaction and volume of sample; thereby diminishing the possibility of error. An additional advantage of the present method is that convection currents introduce far less error than in the case of coated tubes. Convection currents within the coated tube may be extremely difficult to eliminate, yet, when present, they may introduce variations as great as ten-fold in reactions conducted in coated tubes. Solid phase reactants affixed to the surface of the solid phase matrix of the present invention are present in the solution in a uniform and reproducible geometrical relationship in sharp contrast with the situation presented when a reactant is affixed to the surface of a particulate support material, as for example, glass beads. A reactant affixed to the solid phase matrix of the present invention has no tendency to settle out, does not need to be constantly agitated or resuspended and its geometrical relationship with the solution is reproducible from one experiment to the next. An additional advantage of the solid phase matrix system of the present invention over systems employing particulate solid phase supports such as glass beads is the ease with which the solid phase may be separated from the solution at the end of the reaction, without the need for any centrifugation steps.

In addition to the above-cited advantages of the solid phase matrix of the present invention in quantitative and qualitative analysis, there are production advantages of commercial significance. In particular, techniques for immobilizing the fixed component can be adapted to apply to a large number of solid phase matrices at the same time, either in a batchwise or continuous manufacturing process. The consequent economies of scale and increased uniformity of product are clearly advantageous.

DETAILED DESCRIPTION

In the process of the present invention, a solid phase reaction is carried out using one reaction component fixed to the surface of a solid phase matrix which is wetted with a fluid sample containing a mobile component which is to be detected. The reaction is readily initiated by placing the fluid sample into a receptacle containing the solid phase matrix. The fluid sample may be buffered or diluted to extend the relative volume of the sample to reduce errors caused by manipulation of small volume samples that occur in certain prior art techniques discussed supra and to insure constant volume operation.

After incubation of the fluid sample in contact with the solid phase matrix for a given time interval, the amount of the mobile component which has reacted with the solid phase may be quantitatively measured. The matrix may also be used for qualitative assays to the "yes, no" type known in the prior art.

Solid phase reaction kinetics are more complex than the reaction kinetics of homogeneous phase reactions. A detailed theoretical basis for optimizing assay performance as a function of solid phase matrix geometry is not available. However, certain basic considerations of a general nature can be taken into account. The total surface area of the fixed component in contact with the solution is an important factor. The larger the area, the greater the amount of fixed component which may be present in the reaction. Increasing the effective concentration of either the fixed or mobile component will generally increase the over-all reaction rate. Since the amount of the fixed component is determined by the area of the solid phase, the reaction rate should vary as a function of the surface to volume ratio. An increased surface to volume ratio is achieved in the present invention by providing a solid phase matrix which has an increased surface area relative to that available on the inner surface of coated tube assay systems. Moreover, the reaction rate may be a function of the average diffusion distance between the mobile and fixed reactants. Transfer of mobile reactants to the reactive surface may be facilitated by decreasing the average distance between mobile reactants and the reactive surfaces.

Figure 1:
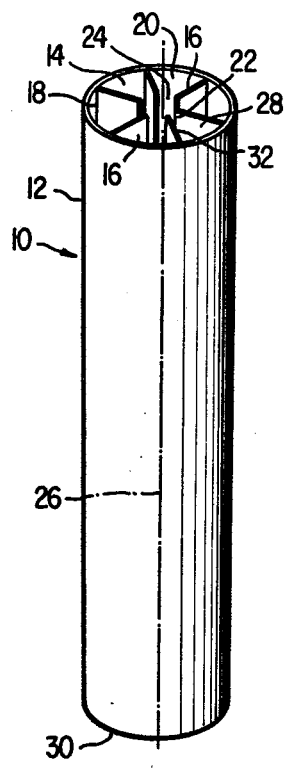
FIG. 1 illustrates the preferred geometric form of a solid phase matrix constructed in accordance with the invention.
Figure 2:
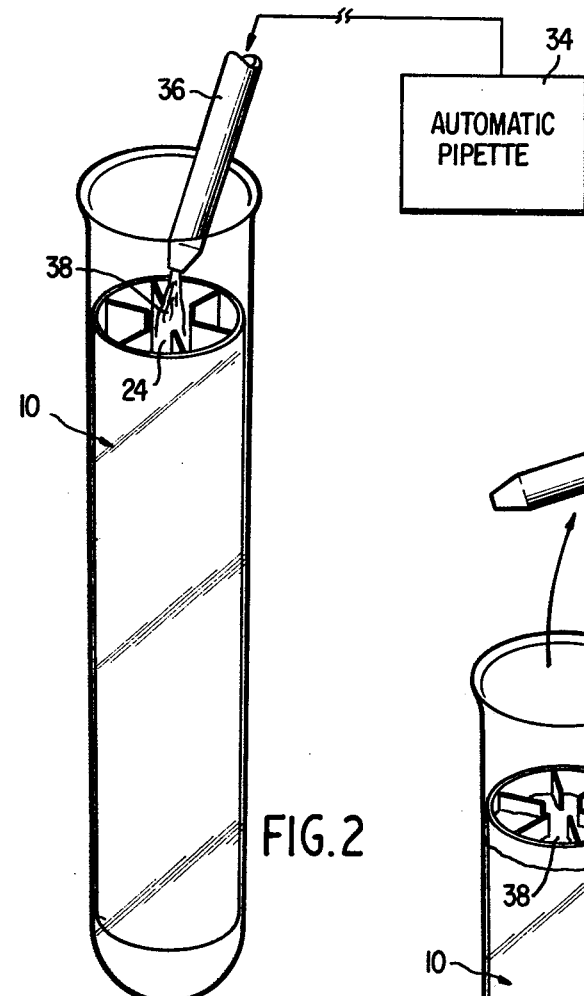
FIG. 2 illustrates a solid phase matrix in accordance with FIG. 1 during the addition of a fluid sample by an automatic pipetting apparatus.
Figure 3:
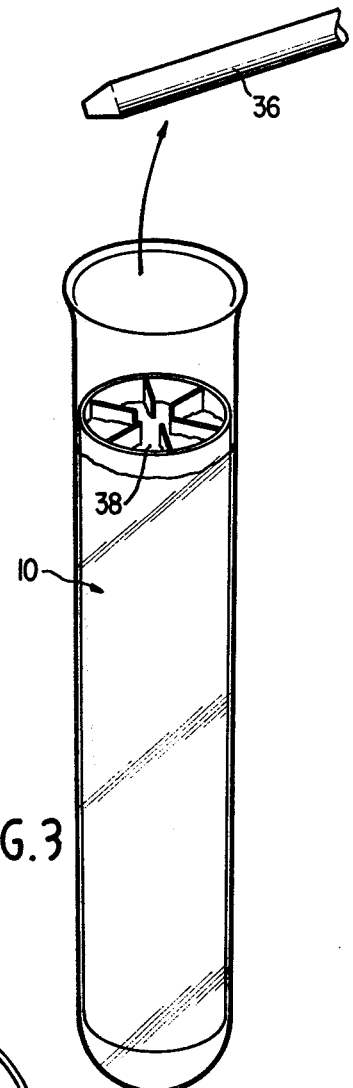
FIG. 3 illustrates the solid phase matrix of FIG. 1 during incubation of the fluid sample.

FIG. 1 illustrates the preferred geometric form of a solid phase matrix which has special utility for use in conjunction with commercially available automatic pipetting apparatus having the capability of aspirating, dispensing and mixing precisely metered fluid volumes. Precise volumetric metering of samples permits the maintenance of proper laboratory control on variables such as volume, buffering and dilution. The solid phase matrix of the invention also facilitates the rapid and precise metering of samples by an automatic pipetting apparatus, thereby contributing to high laboratory productivity and reliability. The solid phase matrix 10 has a support surface 12 which defines a cylindrical well-like region 14 which will be filled with a fluid sample when the matrix is placed in a test tube (FIGS. 2 and 3). A plurality of radially inwardly projecting members 16 each have their outer end 18 joined to the inner face 20 of the support surface. The projecting members 16 and the support surface 12 are preferrably formed by molding or extrusion as a unitary structure or, alternatively, may be formed as separate pieces which are attached together by suitable joining techniques such as a tongue and groove or by an adhesive. The inner ends 22 of the projecting members 16 define a centrally disposed cylindrical region 24 which permits the rapid ingress and egress of a probe of an automatic pipetting apparatus into the bottom of a test tube which contains the matrix as illustrated in FIG. 2 discussed infra. The radially projective surfaces are disposed in planes which intersect the center axis 26 of the centrally disposed cylindrical region. While six projective surfaces have been illustrated, any number may be used. The greater the number of projections, the greater the reactive surface area and, hence, the faster the reaction time. The upper end 28 and the lower end 30 of the support surface are open to permit manufacturing by extrusion as a unitary insert or a molded elongated section which may be cut into uniform lengths. The contour of the bottom end 30 may be rounded to conform to the bottom of a test tube. The top 32 of each projecting member 16 may be sloped downward toward the center line 26 to facilitate sample drainage from a test tube which contains the solid phase matrix.

FIG. 2 illustrates the insert 10 of FIG. 1 being used in conjunction with an automatic pipetting apparatus 34 to perform an assay requiring precise metering of sample volume to maintain proper laboratory control. While the automatic pipetting apparatus is illustrated as a device having a hand-held probe 36 used for aspirating, dispensing and mixing of fluid samples, it is to be understood that fully automated pipetting systems not requiring hand manipulation of a hand-held probe are also intended to be used in conjunction with the solid phase matrix of the invention. In fact, the greatest laboratory productivity using the present invention may be achieved by the use of a fully automated pipetting system used to inoculate a plurality of solid phase matrices positioned in a rack or other suitable holder. The handheld probe 36 of the automatic pipetting apparatus is introduced into the bottom of the cylindrical volume 24 to dispense a predetermined accurately metered volume of sample 38 which is sufficient to completely wet the entire surface area of the solid phase matrix. For purposes of illustration, the probe 36 is adding a fluid sample while being disposed outside of centrally disposed cylinder 24. However, it is to be understood that in actuality, the probe 36 is intended to be introduced down into the cylindrical region 24 to achieve spill-free, nonfoaming addition of samples to wet all of the surface of the matrix 10. The fluid 38 during addition should have sufficient velocity upon dispensing from probe 36 to cause vigorous agitation without foaming. The automatic pipetting apparatus may be any one of the MICROMEDIC series of automatic pipettes manufactured by Rohm & Haas, or apparatus of similar design or function.

The assay technique of the present invention which utilizes a relatively large matrix surface area and a relatively large sample volume has a fast reaction time, is less susceptible to errors encountered when small volumes are used, has high productivity and does not require the expenditure of large sums of money to manufacture the matrix since any water-insoluble, inert; inexpensive material such as polymethacrylate, polypropylene or polystyrene may be used.

FIG. 3 illustrates the incubation of the fluid sample 38 after the withdrawal of the probe 36. The incubation period is chosen to react the fixed component and the mobile component to a degree that either accurate quantitative or qualitative measurements can be made in accordance with the techniques discussed supra.

Figure 4:
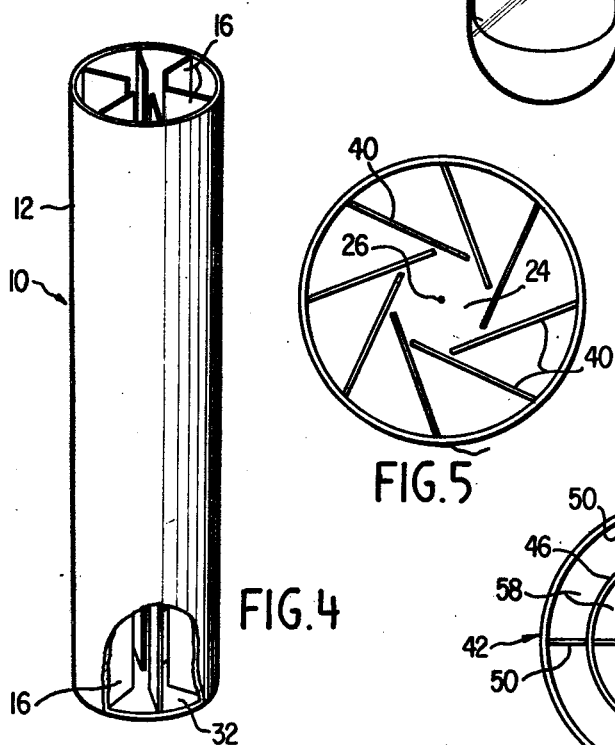
FIG. 4 illustrates another embodiment of a solid phase insert constructed in accordance with the invention having a closed bottom to form a closed fluid receptacle.

FIG. 4 illustrates a modification of the matrix illustrated in FIG. 1 having its lower end 30 closed by bottom section 32 to form a receptacle for fluid consisting of support surface 12 and bottom section 32. The partial sectional view illustrates the bottom section 32 and the projecting members 16. The bottom section 32 is preferably flat to make the matrix freestanding. In this embodiment, assays are carried out without insertion of the matrix into a test tube since the fluid sample is self-contained within the matrix. Instead, the fluid sample is placed directly within the fluid receptacle which has been coated with the fixed component. The use of test tubes in this embodiment is eliminated, thereby eliminating the time-consuming task of insertion and removal of the matrices from the test tubes and cleaning requirements.

Figure 5:
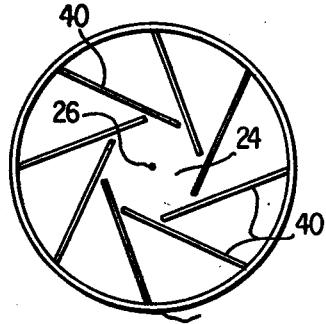
FIG. 5 illustrates a modification of the spatial orientation of the inward projecting members of FIGS. 1-4.

FIG. 5 illustrates a modification of the projecting members 16 of FIG. 1. To increase reactive surface area by inclusion of a greater number of projecting members, the projecting members 40 may be disposed in planes which do not project radially inward to intersect the center axis 26 of central cylindrical region 24. The location of the projecting members in non-radial planes permits maximizing of the reactive surface area. All other parts of this embodiment are identical to FIG. 1.

Figure 6:
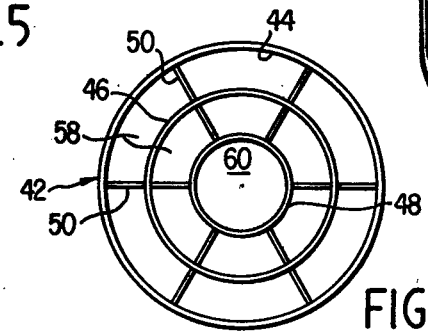
FIG. 6 illustrates a top view of a modification of the solid phase matrix illustrated in FIG. 1 having a plurality of concentrically disposed support surfaces.

FIG. 6 illustrates a top view of a solid phase matrix 42 which is a modification of the solid phase matrix of FIG. 1. The solid phase matrix has a plurality of concentric support surfaces 44, 46 and 48 of decreasing diameter joined together by projecting members 50. The outer end 52 of each projecting member 50 is joined to the inner surface 54 of the outer support surface 44. The inner end 56 of each projecting member 50 is joined to the innermost support surface 48. One or more intermediate support surfaces 46 are joined to the projecting members 50 at points disposed between outer and inner ends 52 and 56. This geometric configuration has increased reactive surface area which is wetted by the sample being assayed when compared with the solid phase matrix of FIG. 1. The concentric support surfaces 44, 46 and 48 of decreasing diameter and projecting members 50 define a plurality of non-centrally disposed well-like region 58 and centrally disposed well-like cylindrical region 60 which extend the entire axial length of the matrix. Centrally disposed region 60 permits the ingress and egress of a probe of an automatic pipetting apparatus in the same manner as illustrated in FIG. 2. The bottom of solid phase matrix 42 (not shown) may be open or have a bottom section which forms a fluid receptacle with the support surfaces 44, 46 and 48. The bottom section may be identical to bottom section 32 illustrated in FIG. 4. The projecting surfaces 50 may be disposed in planes which either intersect or do not intersect the center axis of centrally disposed region 60. If the projecting planes do not intersect the center axis of region 60, they may have a configuration similiar to that illustrated in FIG. 5.

The following examples illustrate the use of the disclosed invention.

EXAMPLE 1

A quantitative assay for an antigen present in serum is carried out using the solid phase matrix of FIG. 1 coated with an antibody immunologically specific for the antigen to be measured. The serum sample to be tested is diluted with buffer and a sufficient volume of this solution is added to a test tube to cover the solid phase matrix contained thereon. $^{125}$I-labeled antigen is added last. The addition of the fluid sample and the $^{125}$I-labeled antigen is carried out by the use of an automatic pipetting system such as one of the MICROMEDIC pipettes to deliver precisely metered volumes of liquid from bulk storage sources. The addition of the fluid sample and $^{125}$I-labeled antigen is in accordance with FIG. 2.

After adding the reactants, the probe is removed (FIG. 3) and the reactants are incubated together at room temperature for an appropriate time period. At the end of incubation, the reaction is terminated by decanting the reaction mixture or aspirating the mixture with the probe of the automatic pipetting system. Any residual material which may have adhered to the walls can be removed by a brief rinse with water or buffer. The tube and insert are then placed in a gamma counting chamber to determine the amount of radioactive antigen bound thereto. The amount of antigen present originally in the serum sample is calculated by reference to a standard curve.

EXAMPLE 2

The use of the solid phase matrix of FIG. 1 of the present invention in a sandwich assay for quantitative determination of an antigen is described. The surface of the matrix is coated, by any method known in the art, including adsorption and covalent binding, with an antibody against the substance to be measured. The first-stage binding reaction is initiated by adding an appropriately buffered dilution of serum to the tube containing the solid phase matrix. If an automatic pipetting device such as the MICROMEDIC (trademark Rohm & Hass Company) is used, serum from individual sample tubes and buffer from a buffer reservoir may be accurately pipetted into the reaction tube.

The reactants are incubated for an appropriate time sufficient to provide substantial binding of the unknown. The reaction mixture is then removed from the reaction tube, the matrix is briefly washed and reagent solution is then added either manually or automatically by an automatic pipetting device. The reagent contains an antibody against the antigen to be measured, and at least a portion of the antibody contains an $^{125}$I-labeled substituent. The reagent is provided in substantial excess amount over the amount of antigen bound to insure that the reagent will bind at most sites where antigen is bound.

At the conclusion of the reagent binding step, the reagent is removed from the reaction tube, the matrix is rinsed briefly and placed in the counting chamber of a gamma counter for determination of bound radioactivity. The amount of radioactivity bound is proportional to the amount of antigen bound which in turn is proportional to the amount of antigen present in the serum sample. Quantitation in units of mass is made by reference to a standard curve.

EXAMPLE 3

A qualitative assay to detect the presence of an antigen is carried out using the solid phase matrix of the present invention of FIG. 1. Reaction conditions of Example 2 are used except that the incubation time for the first step incubation is reduced. The time is so chosen that a positive response over background level is detectable at the desired level of sensitivity.

EXAMPLE 4

The solid phase matrix of FIG. 1 is employed in a quantitative assay of the type described in U.S. Pat. No. 4,020,151. In this assay method, the solid phase matrix does not have antibody immobilized on the surface. The sample to be measured is diluted with buffer and "buffer protein" as in the above-described reference and then added to a test tube containing the solid phase matrix. The reaction tube is then agitated for a period of time sufficient to permit adsorption of the protein to be measured on the matrix surface.

The sample solution is then removed, the matrix surface is washed briefly and an excess of antibody to the protein to be measured is added, in a buffered solution, to the reaction tube. A fluorescent tag such as fluorescein isothiocyanate, as described in the above-cited reference, may be used to label the specific antibody.

After an incubation period sufficient to provide substantially complete binding of the specific antibody, the antibody solution is removed, the tube is washed and the fluoroescence intensity of bound antibody is measured in a fluorometer. The quantity of antigen initially present is determined by reference to a standard curve.

The above examples illustrate the use of the solid phase matrix of the present invention in conjunction with particular assays. These examples are not intended to limit the field of use in which the solid phase matrix may be used. Accordingly, the invention may be used with any type of qualitative or quantitative solid phase assay without limitation.

Numerous modifications may be made to the geometric forms of the invention described above. The projecting members 16 or 50 may be curved as they project inward. Each projecting member 16 or 50 may have apertures or protuberances or any geometric configuration which increases the reactive surface area and permits fluid to readily drain under influence of gravity. The support surfaces 12 or 44, 46 and 48 may have any geometric shape which permits the projecting members 16 or 50 to be attached thereto or formed as a unitary structure therewith. The volumes 24 or 60 may have any geometric shape which facilitates the insertion of a probe of an automatic pipetting apparatus.

What is claimed is:

1. A solid-phase water-insoluble matrix for use in detecting a mobile component contained in a liquid sample which reacts with a reaction component immobilized on the surface of the matrix to produce a measurable change which is an indication of the presence of the mobile component, said matrix comprising:
   (a) a liquid receptacle having a side wall and a bottom section for retaining liquid samples and an open top for permitting the aspiration, dispensing, decantation and mixing of liquid samples from within the liquid receptacle,
   (b) a plurality of water-insoluble inwardly projecting members having first and second ends, the first end of each projecting member being joined to the inside of the side wall and the second ends of the inwardly projecting members so arranged that the second ends define a second generally cylindrical region centrally located within the liquid receptacle in which apparatus for pipetting liquid may be inserted, said members being so spaced from each other as to permit liquid sample removal by decantation or aspiration, and
   (c) a reaction component immobilized on the surfaces of said matrix, said component selected from the group consisting of antigens, antibodies, enzymes and substrates and being capable of reacting specifically with said mobile component at a rate or to an extent measurable as a function of the concentration of said molecules of a mobile component, whereby said immobilized component undergoes a measurable change or catalyzes a measurable change as a result of said specific reaction.

2. The solid phase matrix of claim 1 wherein:
   the projecting surfaces are disposed in planes which pass through the center axis of the central region.

3. The solid phase matrix of claim 1 wherein:
   the projecting surfaces are disposed in planes which do not pass through the center axis of the central region.

4. The solid phase matrix of claim 1 wherein:
   the side wall is a cylinder.

5. The solid phase matrix of claim 1 further comprising:
   one or more additional support surfaces joined to the plurality of projecting surfaces at points disposed between the first and second ends.

6. The solid phase matrix of claim 1 wherein:
   one of the one or more additional support surfaces is joined to the projecting surfaces at the second ends.

7. A process for detecting a mobile component contained in a liquid sample by reacting the mobile component with a fixed reaction component disposed on the surface of a solid phase reaction matrix comprising:
   (a) adding a volume of a liquid sample having a mobile component to a water-insoluble solid-phase reaction matrix having an elongated annular support surface closed at one end and open at the other end thereof, the annular surface defining a first region, into which a volume of liquid may be added, and a plurality of inwardly extending projections attached to the inner wall of the support surface, the spacing between said inwardly extending projections being sufficient to permit removal of the liquid sample by decantation or aspiration, the plurality of inwardly extending projections being so arranged that they define a second generally cylindrical region centrally disposed within the first region into which may be inserted a pipetting means for dispensing and removing the liquid sample, the second region being substantially smaller than the first region, the interior of the annular surface and each of the projecting surfaces of said matrix having a reaction component immobilized thereon, said reaction component selected from the group consisting of antigens, antibodies, enzymes and substrates and being capable of reacting specifically with said mobile component at a rate or to an extent measurable as a function of the concentration of the molecules of the mobile component, the volume of liquid sample being added by insertion of the pipetting means into the second region to wet the solid-phase matrix;
   (b) contacting the liquid sample with the inwardly extending and inner annular surfaces of the reaction matrix;
   (c) maintaining the liquid sample in contact with the solid-phase matrix surfaces for a given period of time to react the fixed component with any mobile component present in the liquid sample;
(d) removing the liquid sample from the contact with the solid-phase reaction matrix by decantation or insertion of the pipetting means into the second region; and
(e) detecting if any of the mobile component has reacted with the fixed reaction component disposed on the solid-phase reaction matrix.

8. The process of claim 7 wherein:
the fluid sample has been buffered prior to its addition to the fluid receptacle.

9. The process of claim 7 wherein:
the fluid sample has been diluted prior to its addition to the fluid receptacle.

10. The process of claim 7 wherein:
the detection of the reaction of the mobile component with the fixed component is quantitative.

11. The process of claim 7 wherein:
the detection of the reaction of the mobile component with the fixed component is qualitative.

12. The process of claim 11 wherein:
the qualitative detection is produced by measuring if any of the mobile component has been bound to the surface of the solid phase matrix.

* * * * *

UNITED STATES PATENT OFFICE
CERTIFICATE OF CORRECTION

Patent No. 4,197,287      Dated April 8, 1980

Inventor(s) Roger N. Piasio, David A. Perry, Pangal N. Nayak

It is certified that error appears in the above-identified patent and that said Letters Patent are hereby corrected as shown below:

In the Title, "NITRO" should read -- VITRO --.

Column 1, line 2, "NITRO" should read -- VITRO --.

Column 2, line 57, "resuls" should read -- results --.

Column 3, line 51, "slid" should read -- solid --.

Column 6, line 22, "tne" should read -- the --.

Signed and Sealed this

Eighth Day of July 1980

[SEAL]

Attest:

SIDNEY A. DIAMOND

Attesting Officer      Commissioner of Patents and Trademarks